(12) United States Patent
Buyda et al.

(10) Patent No.: US 12,102,305 B2
(45) Date of Patent: Oct. 1, 2024

(54) ADAPTER ASSEMBLIES AND SURGICAL LOADING UNITS

(71) Applicant: Covidien LP, Mansfield, MA (US)

(72) Inventors: Andriy Buyda, East Haven, CT (US); David M. Chowaniec, Rocky Hill, CT (US); Asa G. DeBlois, New Haven, CT (US)

(73) Assignee: Covidien LP, Mansfield, MA (US)

( * ) Notice: Subject to any disclaimer, the term of this patent is extended or adjusted under 35 U.S.C. 154(b) by 866 days.

(21) Appl. No.: 17/121,834

(22) Filed: Dec. 15, 2020

(65) Prior Publication Data

US 2021/0212672 A1   Jul. 15, 2021

Related U.S. Application Data

(60) Provisional application No. 62/961,245, filed on Jan. 15, 2020.

(51) Int. Cl.
*A61B 17/00* (2006.01)
*A61B 17/072* (2006.01)

(52) U.S. Cl.
CPC ...... *A61B 17/00* (2013.01); *A61B 2017/0046* (2013.01); *A61B 2017/00482* (2013.01); *A61B 2017/00486* (2013.01); *A61B 2017/07285* (2013.01)

(58) Field of Classification Search
CPC ............ A61B 17/00; A61B 2017/0046; A61B 2017/00482; A61B 2017/00486; A61B 2017/07285; A61B 2017/00464; A61B 2017/00473; A61B 2017/00477

USPC ............................................................. 606/1
See application file for complete search history.

(56) References Cited

U.S. PATENT DOCUMENTS

| | | |
|---|---|---|
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| RE34,556 E | 3/1994 | Sjostrom et al. |

(Continued)

FOREIGN PATENT DOCUMENTS

| | | |
|---|---|---|
| AU | 2008229795 A1 | 4/2009 |
| CA | 2451558 A1 | 1/2003 |

(Continued)

*Primary Examiner* — Aaron F Roane

(57) ABSTRACT

An adapter assembly includes an elongate body configured to receive a surgical loading unit and an elongate loading bar coupled to the elongate body and configured to selectively lock the surgical loading unit to the adapter assembly. The elongate loading bar has a distal end defining a slot therein configured for receipt of an articulation link of the surgical loading unit upon an improper insertion of the surgical loading unit into the adapter assembly. With the articulation captured in the slot, rotation of the surgical loading unit toward a fully assembled state with the adapter assembly is resisted.

18 Claims, 7 Drawing Sheets

(56) References Cited

U.S. PATENT DOCUMENTS

| | | |
|---|---|---|
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,122 A | 7/2000 | Sjostrom et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |

(56) References Cited

U.S. PATENT DOCUMENTS

| | | |
|---|---|---|
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,887,559 B2 | 2/2011 | Deng et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 10,314,579 B2 | 6/2019 | Chowaniec et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0320252 A1 | 12/2010 | Viola et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |

(56) References Cited

U.S. PATENT DOCUMENTS

| | | |
|---|---|---|
| 2011/0174099 A1 | 7/2011 | Ross et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| CN | 107019532 A | 8/2017 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |
| EP | 2462880 B1 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2839787 A1 | 2/2015 |
| EP | 3165179 A1 | 5/2017 |
| ES | 2333509 A1 | 2/2010 |
| JP | 08038488 | 2/1996 |
| JP | 2005125075 A | 5/2005 |
| KR | 20120022521 A | 3/2012 |
| NO | 2009039506 A1 | 3/2009 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A2 | 11/2003 |
| WO | 2004107989 A1 | 12/2004 |
| WO | 2006042210 A2 | 4/2006 |
| WO | 2007016290 A2 | 2/2007 |
| WO | 2007137304 A2 | 11/2007 |
| WO | 2008131362 A2 | 10/2008 |
| WO | 2008133956 A2 | 11/2008 |
| WO | 2007014355 A3 | 4/2009 |
| WO | 2009132359 A2 | 10/2009 |
| WO | 2009143092 A1 | 11/2009 |
| WO | 2009149234 A1 | 12/2009 |
| WO | 2011108840 A2 | 9/2011 |
| WO | 2012040984 A1 | 4/2012 |

ADAPTER ASSEMBLIES AND SURGICAL LOADING UNITS

CROSS-REFERENCE TO RELATED APPLICATIONS

This application claims the benefit of and priority to U.S. Provisional Patent Application Ser. No. 62/961,245 filed Jan. 15, 2020, the entire disclosure of which is incorporated by reference herein.

FIELD

The present technology is generally related to adapter assemblies for use with an electromechanical surgical system and their methods of use. More specifically, the present technology relates to electromechanical surgical instruments configured to ensure the proper connection of a loading unit with an adapter assembly.

BACKGROUND

Linear clamping, cutting, and stapling surgical devices may be employed in surgical procedures to resect tissue. Conventional linear clamping, cutting, and stapling devices include a handle assembly, an adapter assembly extending from the handle assembly, and a surgical loading unit detachably coupled to the adapter assembly. The surgical loading unit includes a pair of opposing gripping jaw members, which clamp about the tissue. One or both of the jaw members, such as the anvil portion, moves or pivots relative to the overall structure. Actuation of the device may be controlled by a grip trigger maintained in the handle assembly or via a robotic assembly.

In addition to the jaw members, the surgical loading unit may also include a stapling mechanism. One of the jaw members of the surgical loading unit may include a staple cartridge receiving region and a mechanism for driving staples up through tissue clamped against the anvil portion, thereby sealing the tissue. The jaw members may be integrally formed with the adapter assembly or may be detachable such that various gripping and stapling elements may be interchangeable.

SUMMARY

The techniques of this disclosure generally relate to adapter assemblies for interconnecting handle assemblies and surgical loading units. The present disclosure also relates to mechanical features that ensure a proper assembly of the surgical loading unit with the adapter assembly.

According to an aspect of the present disclosure, a surgical instrument is provided and includes a surgical loading unit and an adapter assembly. The surgical loading unit has a proximal body portion, a pair of surface features extending outwardly from the proximal body portion, an articulation link slidably coupled to the proximal body portion, and a tool assembly coupled to a distal end portion of the proximal body portion. The articulation link has a distal end portion coupled to the tool assembly and configured to articulate the tool assembly relative to the proximal body portion. The adapter assembly includes an elongate body and an elongate loading bar coupled to the elongate body. The elongate body has a distal end portion configured to receive the proximal end portion of the proximal body portion of the surgical loading unit. The elongate loading bar is configured to move relative to the elongate body between a proximal position and a distal position and has a distal end defining a slot therein. The slot is configured for receipt of a proximal end portion of the articulation link of the surgical loading unit upon an improper insertion of the surgical loading unit into the adapter assembly, whereby the engagement of the proximal end portion of the articulation link with the slot of the elongate loading bar resists rotation of the surgical loading unit relative to the adapter assembly toward an assembled state.

In aspects, the distal end portion of the elongate body may have an inner surface defining an opening, a pair of diametrically opposed apertures, and a slot. The opening may be configured for receipt of the proximal end portion of the proximal body portion of the surgical loading unit. The pair of diametrically opposed apertures may be configured for receipt of the pair of surface features of the surgical loading unit. The slot may be configured for receipt of the articulation link of the surgical loading unit during a proper insertion of the surgical loading unit into the adapter assembly.

In aspects, the elongate loading bar may have a distal extension configured to selectively lock the surgical loading unit to the adapter assembly when the elongate loading bar is in the distal position.

In aspects, a first surface feature of the pair of surface features may be configured to engage the distal extension of the elongate loading bar to move the elongate loading bar towards the proximal position during a proper insertion of the surgical loading unit into the adapter assembly.

In aspects, the distal extension of the elongate loading bar may be configured for locking engagement with the first surface feature of the surgical loading unit upon the proper insertion and rotation of the surgical loading unit into the elongate body of the adapter assembly.

In aspects, the adapter assembly may further include an annular member rotatably disposed within the distal end portion of the elongate body. The annular member may include a first surface feature configured to interface with a second surface feature of the pair of surface features of the surgical loading unit, such that the annular member is rotatable by the surgical loading unit when the second surface feature of the surgical loading unit is engaged with the first surface feature of the annular member.

In aspects, the annular member may include a second surface feature engaged with the distal extension of the elongate loading bar when the elongate loading bar is in the distal position, such that the distal extension of the elongate loading bar resists rotation of the annular member when the elongate loading bar is in the distal position.

In accordance with another aspect, an adapter assembly is provided and includes an elongate body and an elongate loading bar coupled to the elongate body. The elongate body includes a distal end portion configured to receive a surgical loading unit. The elongate loading bar is configured to move relative to the elongate body between a proximal position, in which the surgical loading unit is removable from the elongate body, and a distal position, in which the elongate loading bar locks the surgical loading unit to the elongate body. The elongate loading bar has a distal end defining a slot therein configured for receipt of an articulation link of the surgical loading unit upon an improper insertion of the surgical loading unit into the adapter assembly, whereby the engagement of the articulation link with the slot of the elongate loading bar resists rotation of the surgical loading unit relative to the adapter assembly toward an assembled state.

In aspects, the distal end portion of the elongate body may have an inner surface defining an opening, a pair of apertures in communication with the opening, and a slot in communication with the opening. The opening may be configured for receipt of the surgical loading unit. The apertures may be configured for receipt of a pair of surface features of the surgical loading unit. The slot may be configured for receipt of the articulation link of the surgical loading unit during a proper insertion of the surgical loading unit into the adapter assembly.

In aspects, the slot of the elongate body may be disposed between the pair of apertures.

In aspects, the slot of the distal end of the elongate loading bar may have substantially the same width as the slot of the elongate body.

In aspects, the elongate loading bar may have a distal extension configured to selectively lock the surgical loading unit to the adapter assembly when the elongate loading bar is in the distal position.

In aspects, the adapter assembly may further include an annular member rotatably disposed within the distal end portion of the elongate body. The annular member may include a first surface feature defining a cavity configured to interface with a lug of the surgical loading unit, such that the annular member is rotatable by the surgical loading unit when the lug of the surgical loading unit is captured in the cavity of the annular member.

In aspects, the annular member may include a second surface feature engaged with the distal extension of the elongate loading bar when the elongate loading bar is in the distal position, such that the distal extension of the elongate loading bar resists rotation of the annular member when the elongate loading bar is in the distal position.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Aspects of the present disclosure are described herein with reference to the accompanying drawings, wherein.

DETAILED DESCRIPTION

Figure 1:
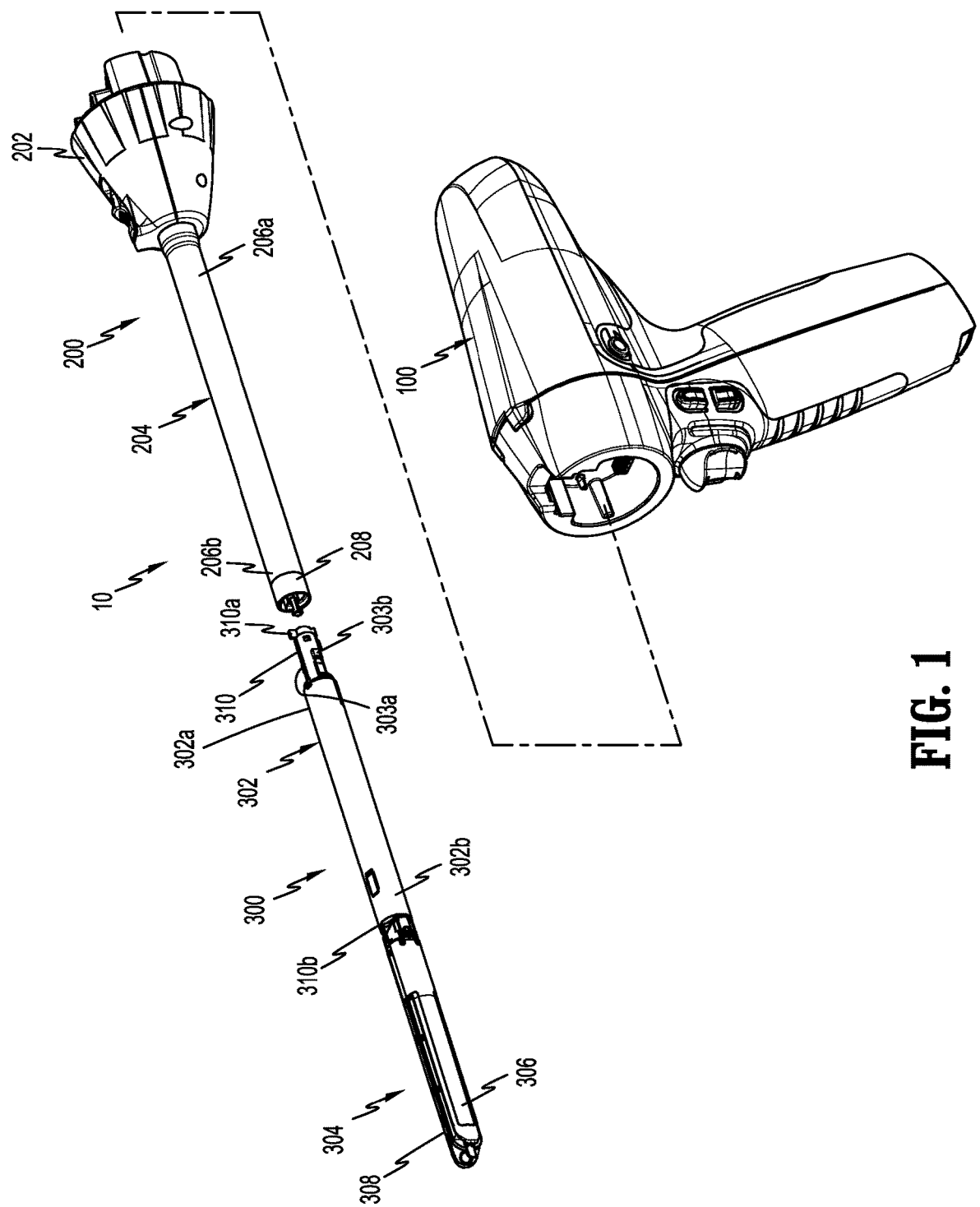
FIG. 1 is a perspective view, with parts separated, of components of a hand-held, electromechanical surgical instrument including a handle assembly, an adapter assembly, and a surgical loading unit.

As used herein, the terms parallel and perpendicular are understood to include relative configurations that are substantially parallel and substantially perpendicular up to about + or −10 degrees from true parallel and true perpendicular.

Aspects of the presently disclosed surgical instruments including handle assemblies, adapter assemblies, and surgical loading units thereof, are described in detail with reference to the drawings, in which like reference numerals designate identical or corresponding elements in each of the several views. As used herein, the term "distal" refers to that portion of the surgical instrument, adapter assembly, handle assembly, loading unit, or component thereof, farther from the user, while the term "proximal" refers to that portion of the surgical instrument, adapter assembly, handle assembly, loading unit or component thereof, closer to the user.

For more details of certain aspects of the adapter assembly disclosed herein, reference may be made to U.S. Pat. No. 10,426,466, the entire contents of which are incorporated by reference herein.

Presently, if a surgical loading unit is inserted incorrectly into an adapter assembly and rotated after the incorrect insertion, an annular member or rotating ring of the adapter assembly is caused to be rotated out of a normal position. After the surgical loading unit is removed, the rotating ring remains out of the normal position. As such, a subsequent attempt at inserting a surgical loading unit into the adapter assembly is prohibited due to the rotating ring being displaced from its normal operating position.

The present disclosure provides a surgical instrument that includes a surgical loading unit and an adapter assembly that interconnects the surgical loading unit with either a handle assembly or a robotic assembly. The adapter assembly includes a plurality of mechanical features that ensure that the surgical loading unit is connected to the adapter assembly in a proper orientation to prevent the improper displacement of the rotating ring.

With reference to FIG. 1, a surgical instrument 10, in accordance with an aspect of the present disclosure, is shown as a powered, hand-held, electromechanical surgical instrument. The surgical instrument 10 includes a handle assembly 100 configured for selective connection with any one of a number of adapter assemblies 200, and, in turn, each unique adapter assembly 200 is configured for selective connection with any number of surgical loading units 300. The surgical loading unit 300 and adapter assembly 200 are configured for actuation and manipulation by the handle assembly 100 or, in aspects, a robotic assembly (not shown).

Figure 2:
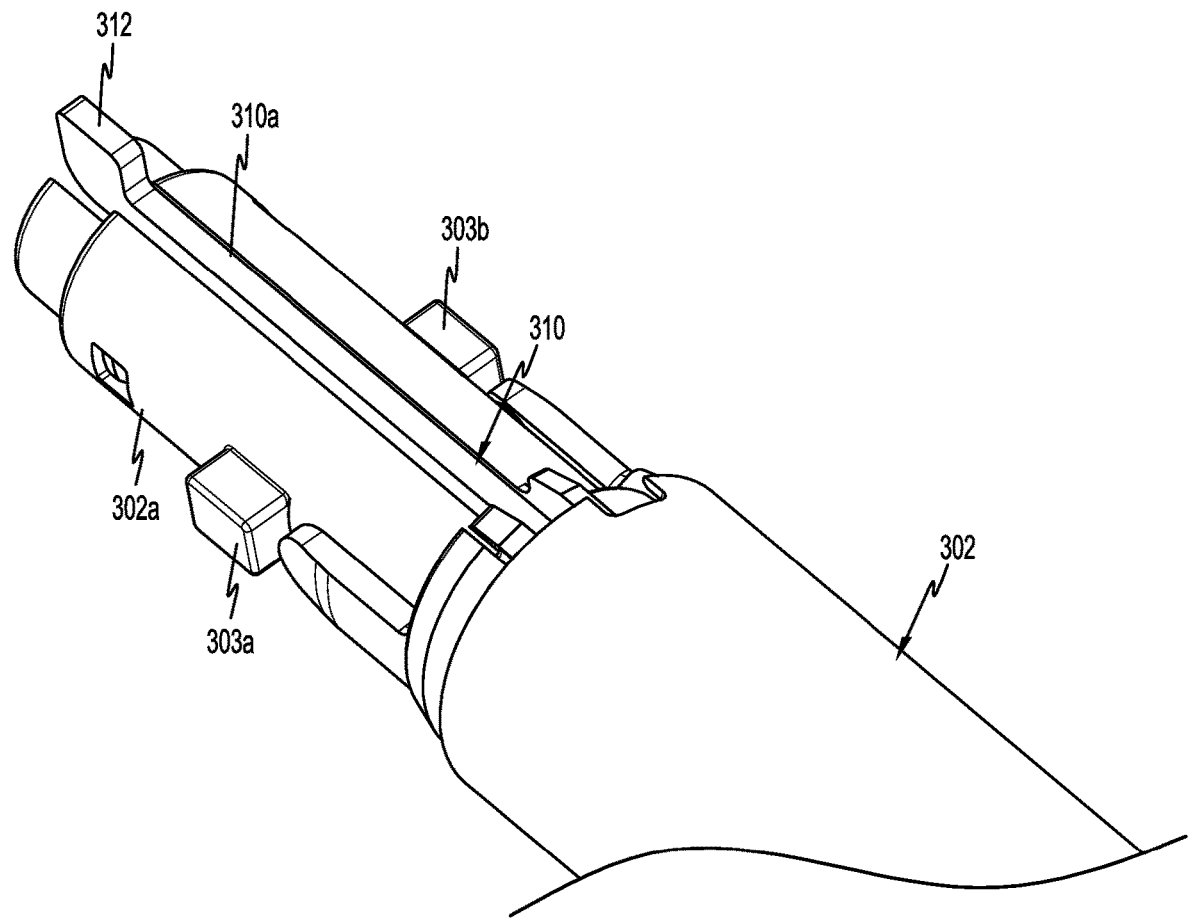
FIG. 2 is a perspective view of a proximal end portion of the surgical loading unit of FIG. 1.

With reference to FIGS. 1 and 2, the surgical loading unit 300 of the surgical instrument 10 has a proximal body portion 302 and a tool assembly or end effector 304 coupled to a distal end portion 302b of the proximal body portion 302. The proximal body portion 302 has a proximal end portion 302a configured for engagement with a distal end portion 206b of an elongate body 204 of the adapter assembly 200. The proximal body portion 302 has a pair of surface features, such as, for example, lugs 303a, 303b extending outwardly from opposite sides of the proximal end portion 302a of the surgical loading unit 300. The lugs 303a, 303b may assume any suitable shape, such as a square or a cylinder. The end effector 304 is pivotally attached to the proximal body portion 302 and includes an anvil assembly 306 and a cartridge assembly 308. The cartridge assembly 308 is pivotable in relation to the anvil assembly 306 and is movable between an open or unclamped position and a closed or clamped position for insertion through a cannula of a trocar. In aspects, the end effector 304 may be configured to perform alternate functions, such as, electrosurgical sealing.

The surgical loading unit 300 further includes an articulation link 310 extending through the proximal body portion 302 and centrally between the lugs 303a, 303b. The articulation link 310 has a proximal end portion 310a having a flag 312 protruding proximally and radially outward from the proximal body portion 302. The flag 312 of the articulation link 310 is configured to operably couple to an articulation drive member (not explicitly shown) of the adapter assembly 200 for driving a translation of the articulation link 310. The articulation link 310 has a distal end portion 310b operably coupled to the end effector 304, such that the end effector 304 is configured to articulate relative to the proximal body portion 302 in response to a translation of the articulation link 310. For example, the end effector 304 is movable from a first position in which the end effector 304 is aligned with a longitudinal axis of the proximal body portion 302 to at least a second position in which the end effector 304 is disposed at a non-zero angle with respect to the longitudinal axis of the proximal body portion 302.

Reference may be made to U.S. Pat. No. 7,819,896, the entire contents of which are incorporated herein by reference, for a detailed discussion of the construction and operation of an exemplary end effector.

With further reference to FIG. 1, the adapter assembly 200 includes a knob housing 202 and an elongate body 204 extending from a distal end of the knob housing 202. The knob housing 202 and elongate body 204 are configured and dimensioned to house the components of the adapter assembly 200. The elongate body 204 may be dimensioned for endoscopic insertion. In aspects, the elongate body 204 may be passable through a typical trocar port, cannula or the like. The knob housing 202 may be dimensioned to not enter the trocar port, cannula of the like. The elongate body 204 has a proximal end portion 206a attached to the knob housing 202, which is configured to be attached to the handle assembly 100. The elongate body 204 also includes a distal end portion 206b configured to be coupled to the proximal body portion 302 of the surgical loading unit 300.

Figure 3:
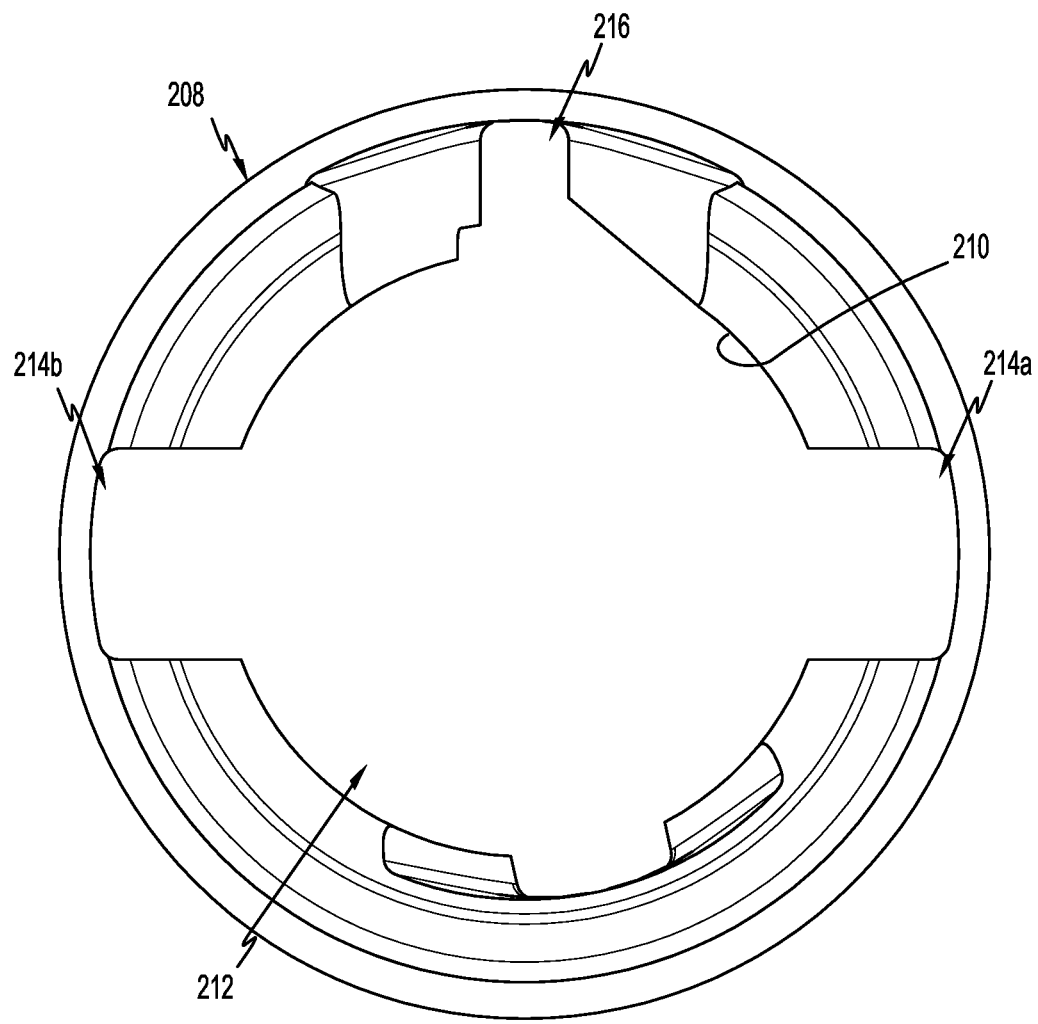
FIG. 3 is a front view of a ring member of the adapter assembly of FIG. 1 which receives the proximal end portion of the surgical loading unit.
Figure 4:
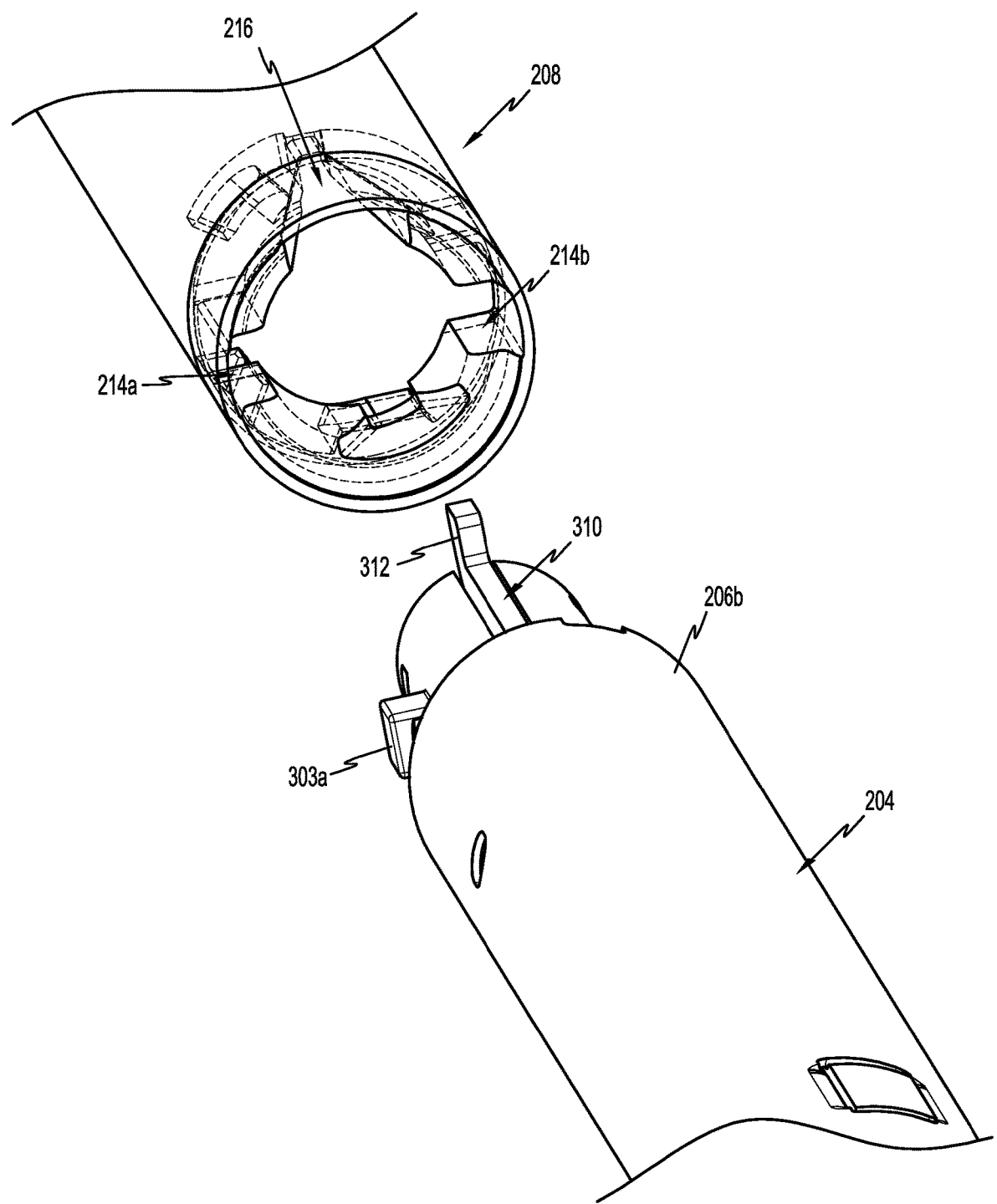
FIG. 4 is a perspective view of the proximal end portion of the surgical loading unit being properly inserted into the ring member of FIG. 3.

With reference to FIGS. 1, 3, and 4, the elongate body 204 of the adapter assembly 200 further includes a distal cap or ring member 208 extending distally from the distal end portion 206b. In aspects, the ring member 208 may be formed with the elongate body 204 and/or may be housed therein. The ring member 208 has an inner surface 210 that defines an opening or channel 212 configured for receipt of the proximal end portion 302a of the proximal body portion 302 of the surgical loading unit 300. The inner surface 210 of the ring member 208 further defines a pair of diametrically opposed apertures 214a, 214b and a slot 216 each being circumferentially disposed about the ring member 208. The slot 216 is disposed between the apertures 214a, 214b and is spaced circumferentially from each of the apertures 214a, 214b by about 90 degrees. The apertures 214a, 214b are configured for receipt of the respective pair of lugs 303a, 303b of the surgical loading unit 300 and the slot 216 is configured for receipt of the proximal end portion 310a (e.g., the flag 312) of the articulation link 310 of the surgical loading unit 300 during a proper insertion of the surgical loading unit 300 into the adapter assembly 200, as shown in FIG. 4.

Figure 5:
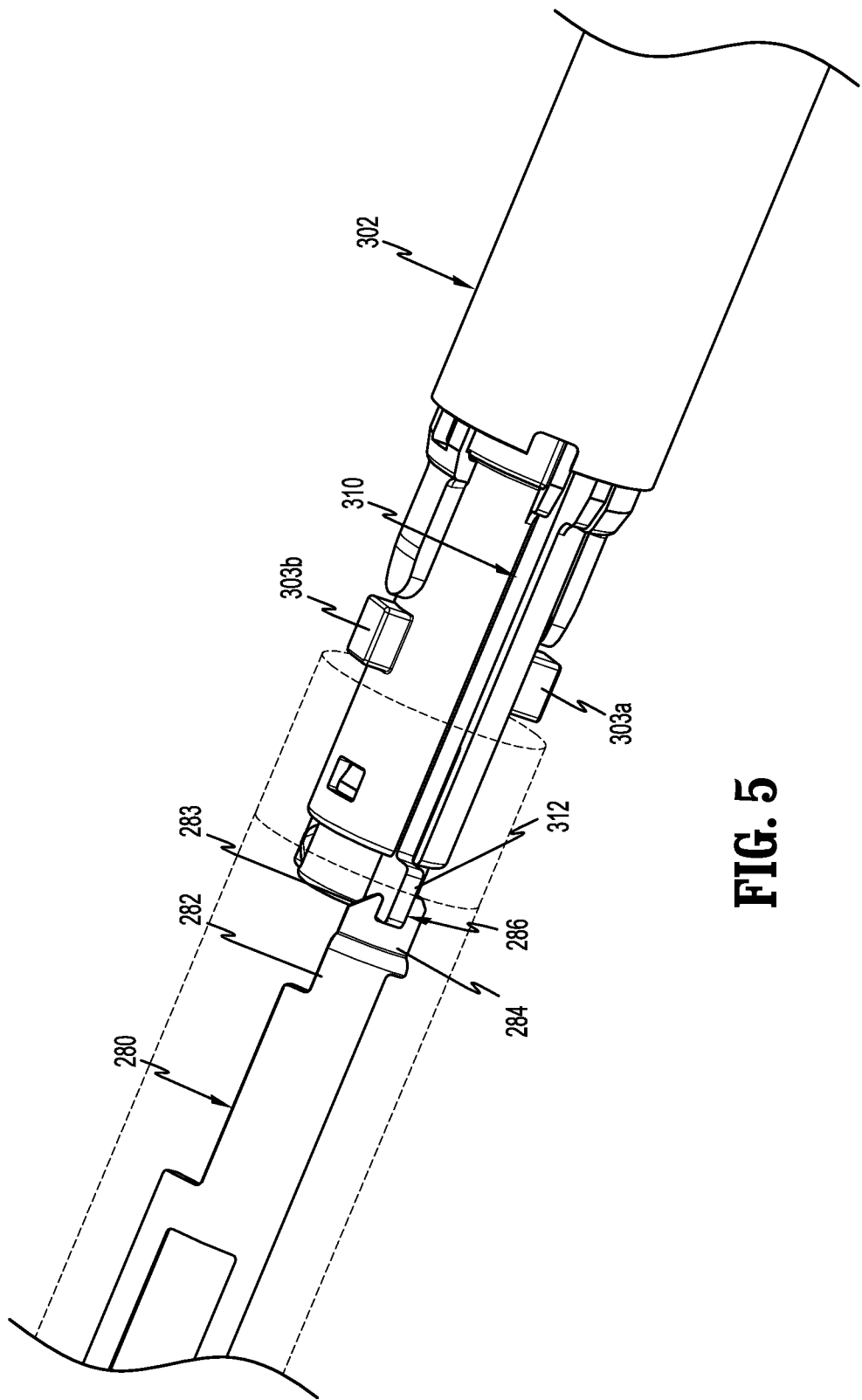
FIG. 5 is a side, perspective view illustrating a first improper insertion of the surgical loading unit into the adapter assembly.
Figure 7:
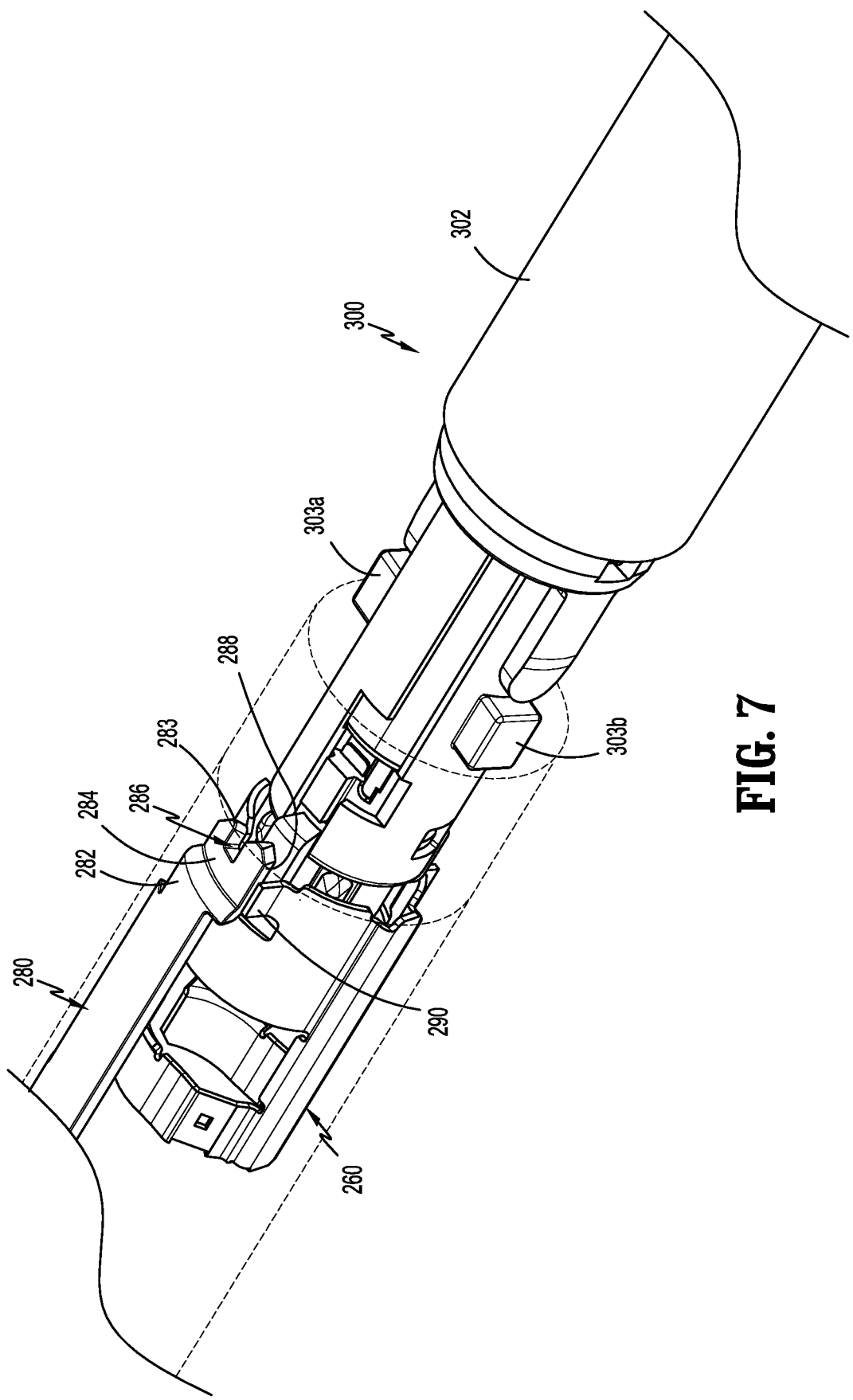
FIG. 7 is a perspective view illustrating another side of the surgical instrument during the second improper insertion of the surgical loading unit into the adapter assembly.

With reference to FIGS. 5 and 7, the adapter assembly 200 further includes an elongate loading bar or locking link 280 disposed within the elongate body 204 of the adapter assembly 200. The elongate loading bar 280 is slidingly disposed within the elongate body 204 and is resiliently biased toward a distal, locking position, as shown in FIG. 5. The elongate loading bar 280 has a distal extension 282 configured for locking engagement with the lug 303a (FIG. 2) of the surgical loading unit 300 upon the proper insertion of the surgical loading unit 300 into elongate body 204. The distal extension 282 has a distal end 284 having a distally-facing edge 283 defining a slot 286 therein. The slot 286 has a similar shape and size as the flag 312 of the surgical loading unit 300 to accommodate the flag 312 therein during an improper insertion of the surgical loading unit 300 into adapter assembly 200 (FIG. 5). The slot 286 as illustrated has a rectangular shape, but other suitable shapes are contemplated, such as rounded, triangular, or the like.

Figure 6:
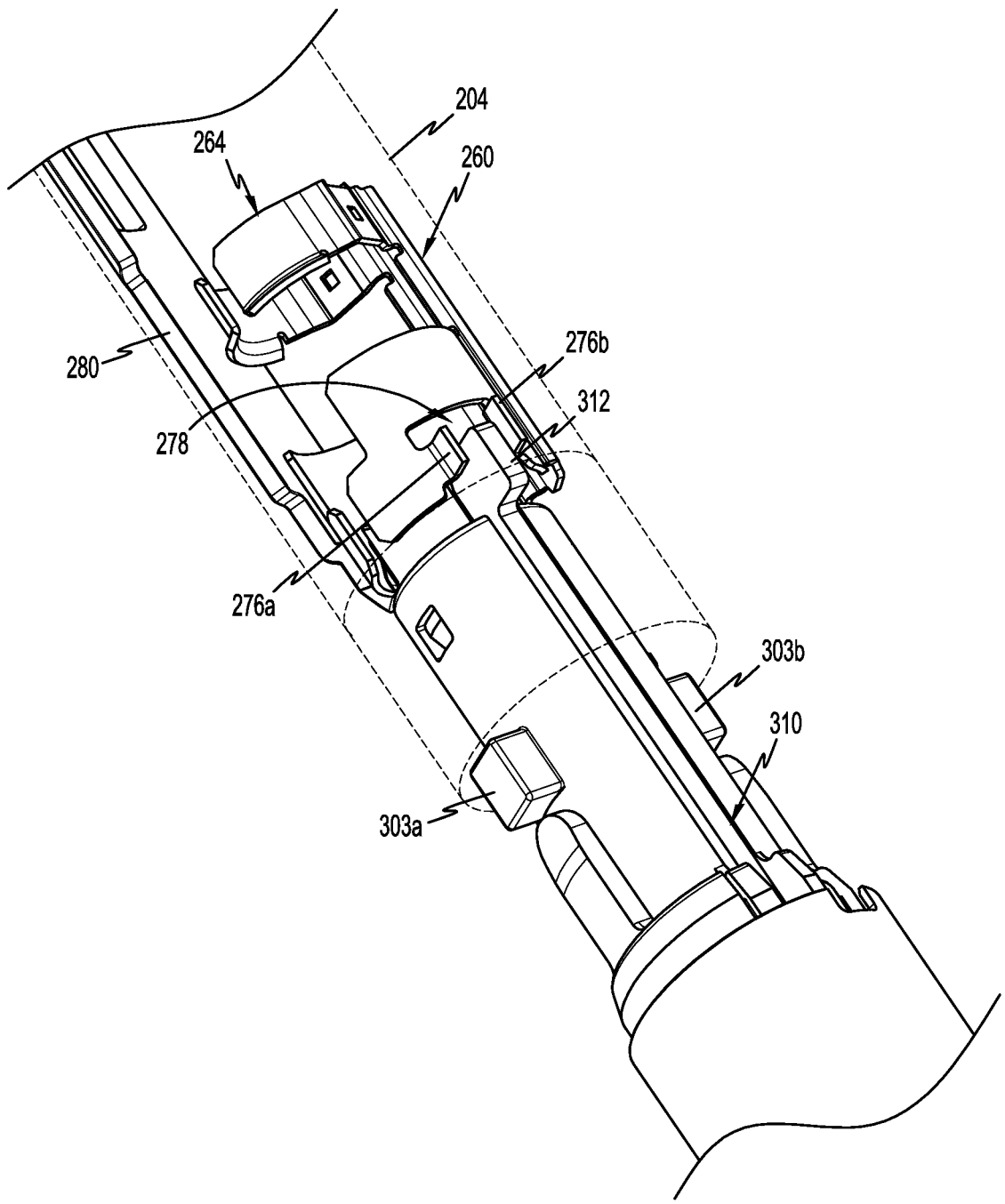
FIG. 6 is a side, perspective view illustrating a first side of the surgical instrument during a second improper insertion of the surgical loading unit into the adapter assembly.

With reference to FIGS. 6 and 7, the adapter assembly 200 further includes an annular member 260 rotatably disposed within the elongate body 204 of the adapter assembly 200. The annular member 260 functions to electromechanically communicate to a processor (not shown) of the handle assembly 100 that the surgical loading unit 300 is either properly or improperly connected to the adapter assembly 200. In particular, upon rotating the annular member 260 relative to the elongate body 204, about a longitudinal axis of the elongate body 204, from a starting or first orientation to a second orientation, the annular member 260 transmits a signal to the processor of the handle assembly 100 indicating that the surgical loading unit 300 is secured to the adapter assembly 200 and is ready for use.

The annular member 260 defines a cylindrical passageway 264 therethrough configured for disposal of the proximal body portion 302 of the surgical loading unit 300. The annular member 260 includes a surface feature, such as, for example, a pair of tabs 276a, 276b defining a cavity 278 therebetween configured to interface with the lug 303b of the surgical loading unit 300, such that the annular member 260 is rotatable by and with the surgical loading unit 300 when the surgical loading unit 300 is properly inserted into the adapter assembly 200.

The annular member 260 further includes an appendage or additional surface feature 290 protruding radially outward therefrom and disposed on an opposite side of the annular member 260 as the pair of tabs 276a, 276b. The appendage or tab 290 is positioned in abutting engagement with a lateral edge surface 288 of the distal extension 282 of the elongate loading bar 280 (FIG. 7) when the elongate loading bar 280 is in the distal position. The elongate loading bar 280 prevents the annular member 260, and in turn, the surgical loading unit 300, from being rotated relative to the elongate body 204 due to the engagement of the appendage 290 of the annular member 260 with the elongate loading bar 280. As such, only when the lug 303a of the surgical loading unit 300 engages and proximally moves the elongate loading bar 280 out of engagement with the appendage 290 (during a proper insertion of the surgical loading unit 300) will the annular member 260 be able to be rotated by the surgical loading unit 300.

In operation, to properly assemble the surgical loading unit 300 with the adapter assembly 200, the surgical loading unit 300 is rotationally oriented (about a longitudinal axis thereof) so that the pair of lugs 303a, 303b of the surgical loading unit 300 are aligned with the pair of apertures 214a, 214b of the ring member 260 and the flag 312 of the articulation link 310 of the surgical loading unit 300 is aligned with the slot 216 of the ring member 208, as shown in FIG. 4. With the surgical loading unit 300 properly oriented, the surgical loading unit 300 may be translated toward the adapter assembly 200 to pass the proximal body portion 302 of the surgical loading unit 300 into the elongate body 204 of the adapter assembly 200 and, in turn, into the annular member 260. Upon fully inserting the surgical loading unit 300 into the adapter assembly 200, the lug 303b of the surgical loading unit 300 is received between the surface features 276a, 276b of the annular member 260, the lug 303a of the surgical loading unit 300 engages the elongate loading bar 280 to retract the elongate loading bar 280 towards its proximal position, and the flag 312 of the articulation link 310 couples to the articulation drive member (not shown) of the adapter assembly 200.

After moving the elongate loading bar 280 to the proximal position by the lug 303a of the surgical loading unit 300, the distal extension 282 of the elongate loading bar 280 is no longer engaged with the appendage 290 of the annular member 260, and therefore no longer preventing the annular member 260 from rotating out of the first orientation. With the surgical loading unit 300 in this initial insertion position within the adapter assembly 200, the surgical loading unit 300 is not yet lockingly engaged with the adapter assembly 200 and the annular member 260 remains in the first orientation. To complete the mechanical coupling of the surgical loading unit 300 to the adapter assembly 200, the surgical loading unit 300 is then rotated relative to the elongate body 204. Since the lug 303b of the surgical loading unit 300 is received in the cavity 278 defined between the surface features 276a, 276b of the annular member 260, rotation of the surgical loading unit 300 drives a rotation of the annular member 260 from the first orientation to the second orientation. Rotation of the annular member 260 from the first orientation to the second orientation establishes an electrical connection between the annular member 260 and the processor of the handle assembly 100, whereby the processor registers that the surgical loading unit 300 is lockingly engaged with the adapter assembly 200 and surgical instrument 10 is ready for operation.

For a more detailed description of the electrical connection between the annular member 260 and the processor, reference may be made to U.S. Pat. No. 10,314,579, the entire contents of which are incorporated by reference herein.

The rotation of the surgical loading unit 300 moves the lug 303a of the surgical loading unit 300 into an inner groove (not explicitly shown) defined in the ring member 208 of the elongate body 204 and out of a longitudinal path of the elongate loading bar 280. The resilient bias of the elongate loading bar 280 drives an axial translation thereof to dispose the elongate loading bar 280 in the distal or locking position. With the elongate loading bar 280 in the distal position, the lug 303a of the surgical loading unit 300 is captured between the ring member 208 and the distal extension 282, thereby preventing the surgical loading unit 300 from sliding or rotating out of the adapter assembly 200. In this state, the surgical loading unit 300 is properly releasably, lockingly engaged to the adapter assembly 200 and ready for use.

In some instances, it is possible for a clinician to inadvertently improperly orient the surgical loading unit 300 (about a longitudinal axis thereof) relative to the adapter assembly 200 prior to inserting the surgical loading unit 300 into the adapter assembly 200. For example, with reference to FIG. 5, the surgical loading unit 300 may be improperly oriented 90 degrees counter-clockwise (about the longitudinal axis thereof) from the proper orientation. When the rotational orientation of the surgical loading unit 300 is improper, the surgical loading unit 300 may still be longitudinally inserted into the adapter assembly 200. However, in this orientation, instead of the lug 303a of the surgical loading unit 300 engaging the distal extension 282 of the elongate loading bar 280, the flag 312 of the articulation link 310 is received in the slot 286 of the distal extension 282. Accordingly, when the clinician attempts to complete the assembly of the surgical loading unit 300 with the adapter assembly 200 by exerting a rotational force on the surgical loading unit 300, the engagement of the flag 312 of the articulation link 310 with the slot 286 of the elongate loading bar 280, which is non-rotatable, advantageously prevents the surgical loading unit 300 from being rotated. Therefore, the clinician will be unable to operate the surgical instrument 10 and will be alerted to the fact that the surgical loading unit 300 is improperly oriented.

With reference to FIGS. 6 and 7, the surgical loading unit 300 may be improperly oriented 90 degrees clockwise (about the longitudinal axis thereof) from the proper orientation. In this orientation, the flag 312 of the articulation link 310 is received in the cavity 278 defined by the pair of surface features 276a, 276b of the annular member 260 instead of the lug 303b of the surgical loading unit 300, as shown in FIG. 6. In addition, neither lug 303a nor lug 303b of the surgical loading unit 300 will engage the distal extension 282 of the elongate loading bar 280, such that the distal extension 282 remains engaged with the appendage 290 of the annular member 260. Accordingly, when the clinician attempts to complete the assembly of the surgical loading unit 300 with the adapter assembly 200 by exerting a rotational force on the surgical loading unit 300, the engagement of the appendage 290 with the distal extension 282 advantageously prevents the annular member 260, and in turn, the surgical loading unit 300 from being rotated. Therefore, the clinician will be unable to operate the surgical instrument 10 and will be alerted to the fact that the surgical loading unit 300 is improperly oriented.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A surgical instrument, comprising:
   a surgical loading unit including:
      a proximal body portion defining a surgical loading unit longitudinal axis;
      a pair of surface features extending outwardly from the proximal body portion;
      an articulation link slidably coupled to the proximal body portion and having a proximal end portion, and a distal end portion; and
      a tool assembly coupled to a distal end portion of the proximal body portion, the distal end portion of the articulation link coupled to the tool assembly and configured to articulate the tool assembly relative to the proximal body portion; and
   an adapter assembly including:
      an elongate body including a distal end portion configured to receive the proximal end portion of the surgical loading unit, the distal end portion of the elongate body defining an adapter assembly longitudinal axis; and an elongate loading bar coupled to the elongate body and configured to move relative to the elongate body between a proximal position and a distal position, wherein engagement of the surgical loading unit with the adapter assembly includes radially orienting the surgical loading unit along the surgical loading unit longitudinal axis and the adapter assembly along the adapter assembly longitudinal axis in one specific radial engagement orientation and inserting the proximal body portion of the surgical loading unit into the distal end portion of the elongate body of the adapter assembly; and wherein the elongate loading bar has a distal end defining a slot therein configured for receipt of a proximal end portion of the articulation link of the surgical loading unit upon insertion of the surgical loading unit into the adapter assembly which is not in the one specific radial engagement orientation, whereby the engagement of the proximal end portion of the articulation link with the slot of the elongate loading bar resists rotation of the surgical loading unit relative to the adapter assembly toward an assembled state.

2. The surgical instrument according to claim 1, wherein the distal end portion of the elongate body has an inner surface defining:
an opening configured for receipt of the proximal end portion of the proximal body portion of the surgical loading unit;
a pair of diametrically opposed apertures configured for receipt of the pair of surface features of the surgical loading unit; and
a slot configured for receipt of the articulation link of the surgical loading unit during insertion of the surgical loading unit into the adapter assembly when in the one specific radial engagement orientation.

3. The surgical instrument according to claim 1, wherein the elongate loading bar has a distal extension configured to selectively lock the surgical loading unit to the adapter assembly when the elongate loading bar is in the distal position.

4. The surgical instrument according to claim 3, wherein a first surface feature of the pair of surface features is configured to engage the distal extension of the elongate loading bar to move the elongate loading bar towards the proximal position during insertion of the surgical loading unit into the adapter assembly when in the one specific radial engagement orientation.

5. The surgical instrument according to claim 4, wherein the distal extension of the elongate loading bar is configured for locking engagement with the first surface feature of the surgical loading unit upon the insertion, when in the one specific radial engagement orientation, and rotation of the surgical loading unit into the elongate body of the adapter assembly.

6. The surgical instrument according to claim 3, wherein the adapter assembly further includes an annular member rotatably disposed within the distal end portion of the elongate body, wherein the annular member includes a first surface feature configured to interface with a second surface feature of the pair of surface features of the surgical loading unit, such that the annular member is rotatable by the surgical loading unit when the second surface feature of the surgical loading unit is engaged with the first surface feature of the annular member.

7. The surgical instrument according to claim 6, wherein the annular member includes a second surface feature engaged with the distal extension of the elongate loading bar when the elongate loading bar is in the distal position, such that the distal extension of the elongate loading bar resists rotation of the annular member when the elongate loading bar is in the distal position.

8. The surgical instrument according to claim 1, wherein the distal end portion of the elongate body of the adapter assembly has an inner surface defining:
an opening configured for receipt of the surgical loading unit;
a pair of apertures in communication with the opening and configured for receipt of a pair of surface features of the surgical loading unit; and
a slot in communication with the opening and configured for receipt of the articulation link of the surgical loading unit during insertion of the surgical loading unit into the adapter assembly when in the specific radial engagement orientation.

9. The surgical instrument according to claim 8, wherein the slot of the elongate body is disposed between the pair of apertures.

10. The surgical instrument according to claim 1, wherein the elongate loading bar has a distal extension configured to selectively lock the surgical loading unit to the adapter assembly when the elongate loading bar is in the distal position.

11. The surgical instrument according to claim 10, further comprising an annular member rotatably disposed within the distal end portion of the elongate body, wherein the annular member includes a first surface feature defining a cavity configured to interface with a lug of the surgical loading unit, such that the annular member is rotatable by the surgical loading unit when the lug of the surgical loading unit is captured in the cavity of the annular member.

12. The surgical instrument according to claim 11, wherein the annular member includes a second surface feature engaged with the distal extension of the elongate loading bar when the elongate loading bar is in the distal position, such that the distal extension of the elongate loading bar resists rotation of the annular member when the elongate loading bar is in the distal position.

13. An adapter assembly comprising:
an elongate body including a distal end portion configured to receive a surgical loading unit, the elongate body defining an adapter assembly longitudinal axis and the surgical loading unit defining a surgical loading unit longitudinal axis, wherein receiving of the surgical loading unit into the adapter assembly includes radially orienting the surgical loading unit along the surgical loading unit longitudinal axis and the elongate body along the adapter assembly longitudinal axis in one specific radial engagement orientation and inserting the surgical loading unit into the distal end portion of the elongate body; and
an elongate loading bar coupled to the elongate body and configured to move relative to the elongate body between a proximal position, in which the surgical loading unit is removable from the elongate body, and a distal position, in which the elongate loading bar locks the surgical loading unit to the elongate body, wherein the elongate loading bar has a distal end defining a slot therein configured for receipt of an articulation link of the surgical loading unit upon insertion of the surgical loading unit into the adapter assembly which is not in the one specific radial engagement orientation, whereby the engagement of the articulation link with the slot of the elongate loading bar resists rotation of the surgical loading unit relative to the adapter assembly toward an assembled state.

14. The adapter assembly according to claim 13, wherein the distal end portion of the elongate body has an inner surface defining:
   an opening configured for receipt of the surgical loading unit;
   a pair of apertures in communication with the opening and configured for receipt of a pair of surface features of the surgical loading unit; and
   a slot in communication with the opening and configured for receipt of the articulation link of the surgical loading unit during insertion of the surgical loading unit into the adapter assembly when in the one specific radial engagement orientation.

15. The adapter assembly according to claim 14, wherein the slot of the elongate body is disposed between the pair of apertures.

16. The adapter assembly according to claim 13, wherein the elongate loading bar has a distal extension configured to selectively lock the surgical loading unit to the adapter assembly when the elongate loading bar is in the distal position.

17. The adapter assembly according to claim 16, further comprising an annular member rotatably disposed within the distal end portion of the elongate body, wherein the annular member includes a first surface feature defining a cavity configured to interface with a lug of the surgical loading unit, such that the annular member is rotatable by the surgical loading unit when the lug of the surgical loading unit is captured in the cavity of the annular member.

18. The adapter assembly according to claim 17, wherein the annular member includes a second surface feature engaged with the distal extension of the elongate loading bar when the elongate loading bar is in the distal position, such that the distal extension of the elongate loading bar resists rotation of the annular member when the elongate loading bar is in the distal position.

\* \* \* \* \*